United States Patent [19]
Shalaby et al.

[11] Patent Number: 6,037,331
[45] Date of Patent: *Mar. 14, 2000

[54] COMPOSITIONS FOR PREVENTION OF INFLAMMATION AND ADHESION FORMATION USES THEREOF

[75] Inventors: Shalaby W. Shalaby, Anderson, S.C.; Julie Miller Hasenwinkel, Riverside, Ill.

[73] Assignee: Poly-Med, Inc.

[ * ] Notice: This patent is subject to a terminal disclaimer.

[21] Appl. No.: 09/190,432

[22] Filed: Nov. 12, 1998

Related U.S. Application Data

[63] Continuation-in-part of application No. 08/684,653, Jul. 19, 1996, Pat. No. 5,866,554.

[51] Int. Cl.[7] ..................................................... A61K 31/70
[52] U.S. Cl. ............................ 514/54; 536/55.1; 514/176
[58] Field of Search ..................... 514/54, 174; 536/55.1

[56] References Cited

U.S. PATENT DOCUMENTS 5,866,554  2/1999  Shalaby ...................................... 514/54

*Primary Examiner*—D. Margaret Seaman
*Attorney, Agent, or Firm*—Wolf, Greenfield & Sacks, P.C.

[57] ABSTRACT

Pharmaceutical compositions comprising hyaluronic acid, non-steroidal inflammatory drugs, and at least one organic salt of at least one divalent metal, and methods of using these compositions for the inhibition of inflammation and adhesion formation are described. Preferred organic salts of divalent metals include magnesium acetate, zinc acetate, calcium gluconate, and ferrous gluconate. A preferred non-steroidal anti-inflammatory drug is cyclosporin A.

20 Claims, 1 Drawing Sheet

COMPOSITIONS FOR PREVENTION OF INFLAMMATION AND ADHESION FORMATION USES THEREOF

CROSS-REFERENCE TO RELATED APPLICATIONS

This application is a continuation-in-part of U.S. application Ser. No. 08/684,653, filed on Jul. 19, 1996 now U.S. Pat. No. 5,866,554.

BACKGROUND OF THE INVENTION

The invention relates to the inhibition or prevention of inflammation and adhesion formation using pharmaceutical compositions containing hyaluronic acid, non-steroidal inflammatory drugs, and at least one organic salt of at least one divalent metal selected from the group consisting of magnesium acetate, zinc acetate, calcium gluconate, and ferrous gluconate.

During the normal healing process in response to tissue trauma, initial damage to the mesothelial layer evokes an inflammatory response which is mediated by activation of the kinin, complement and clotting systems (Stangel et al., *J. Reprod. Med.* 29:143, 1984). A serofibrinous exudate including kinin, prostaglandins, and histamine is produced, which increases the permeability of local blood vessels (Buckman et al., *J. Surg. Res.* 20:1, 1976; Stangel et al., supra). Leukocytes are attracted to the site by chemotaxis and the fibrinous exudate is attracted to the damaged tissue surface due to permeability factors. Fibrin is present in free blood as fibrinogen and it is also a normal product of the clotting cascade. During coagulation, thin strands of fibrinous adhesions form on the damaged surface within the first three hours (Stangel et al. supra). The majority of these fibrinous adhesions are lysed within the first 72 hours as part of the normal healing process and never represent any type of clinical complication for the individual.

In some cases, however, these initial fibrinous adhesions persist and become organized into permanent, thick, fibrous adhesions which represent a significant clinical problem across many different fields of medicine. This phenomenon is often associated with joint disease, accidental trauma, and surgical procedures, and is thought to be triggered by an adverse response to many common stimuli including, for example, an overwhelming inflammatory response, tissue ischemia, and the loss of natural physical tissue separation. For example, post-surgical peritoneal adhesions are one of the leading causes of intestinal blockage or obstruction (Ellis, *Surg. Gynecol. Obstet.* 133:497, 1971), and are also of great concern to surgeons who attempt to improve fertility in women through reconstruction. Pelvic adhesions can impair fertility by interfering with the ability of the fallopian tubes to pick up the ovum (Holtz, *Fertil. Steril.* 41:497, 1984; Diamond and Hershlag, *Prg. Clin. Biol. Res.* 358:23, 1990). The formation of permanent adhesions in tendons and joints is a major cause of decreased mobility and chronic pain.

Most research on adhesion prevention agents pertains to post-surgical abdominal adhesion, and minor efforts have been directed to other adhesions such as those experienced in the thorax and tendons. Some of these studies focused on the prevention of fibrin deposition as a strategy to prevent post-surgical adhesion. These strategies included the use of anticoagulants (Holtz, Prog. Clin. Biol. Res. 381:81, 1993); and irrigation (Tulandi, *Prog. Clin. Biol. Res.* 381:149, 1993); and the separation of tissue surfaces using (a) dextran lavage of intraperitoneal procedures (diZerega, *Prog. Clin. Biol. Res.* 381:1, 1993); (b) oxidized cellulose films, e.g., Interceed (diZerega, supra); (c) carboxymethyl cellulose solution (Elkins et al., *Fertil. Steril.* 41:929, 1984); (d) chondroitin sulfate solutions (Oelsner, *J. Reprod. Med.* 32:812, 1987); (e) polyvinyl pyrrolidine solutions (Goldberg et al., *Arch. Surg.* 115:776, 1980); (f) Polyoxamer 407 solutions (Steinleitner et al., *Obstet. Gynecol.* 77:48, 1991); and (g) Gortex films (Boyers et al., *Prog. Clin. Biol. Res.* 358:93, 1990).

Other approaches to prevent post-surgical adhesions have relied on the (a) removal of fibrin matrix through the use of fibrinolytics and proteolytic enzymes (Kapur et al., *Arch. Surg.* 105:761, 1972; Stangel et al. 1984, supra) or tissue-type plasminogen activator (Evans, Am. J. Surg. 165:229, 1993); and (b) surgical removal of adhesions (Stangel et al. 1984, supra).

Still other strategies have focused on inhibiting the overwhelming inflammatory response to injury which has been found to be one of the key factors in adhesion formation. A variety of pharmacological agents which have anti-inflammatory properties, including corticosteroid, antihistamines, antiprostaglandins, and non-steroidal anti-inflammatory agents have been investigated in terms of their potential as anti-adhesion agents. Of those agents studied, non-steroidal anti-inflammatory drugs (NSAIDs) have been reported to be among the most successful in inhibiting inflammation and adhesions formation (diZerega, *Prog. Clin. Biol. Res.* 381:1, 1993). However, early clinical studies were not as encouraging as expected, based on earlier animal studies. One of the main concerns in administering NSAIDs is the method of delivery. Systemic delivery of the drugs requires sufficient blood supply to the injured site; however, this is often disrupted during surgery. Thus, tissue ischemia not only stimulates adhesion formation it also prevents the effective systematic delivery of NSAIDs (diZerega, 1993 supra). Continuous delivery of the NSAID, tolmetin sodium, was reported to be highly effective in preventing peritoneal adhesions (Rodgers et al., *Int. J. Fertil.* 35:40, 1990). However, continuous drug delivery is impractical in a clinical setting. Therefore, there is a distinct need for appropriate and effective, non-toxic local delivery systems for non-steroidal anti-inflammatory drugs.

Another approach to adhesion prevention which has met with a certain degree of success entails the use of hyaluronic acid. Hyaluronic acid has been tested in several different model systems to determine its efficacy in preventing adhesion formation and reformation. There is extensive literature on the use of HA solutions to reduce postoperative adhesion formation following abdominal and orthopedic surgery. Although the results of various studies have been somewhat contradictory, there appears to be a consensus that to achieve significant biological efficacy, HA compositions must be of high viscosity, high HA concentration, and must contain high molecular weight and highly conformationally ordered HA molecules (Balazs, U.S. Pat. No. 4,141,973). However, these properties limit the practical use of such HA solutions, especially in methods requiring injection of the compositions into small spaces (e.g., tendon sheaths, joints) because, generally, solutions containing high concentrations of HA having a molecular weight greater than $8 \times 10^5$ Daltons are not suitable for use as injectable formulations.

In a recent study, Abe et al. (*J. Surg. Res.* 55:451, 1990) evaluated the efficacy of sodium tolmetin in a medium of hyaluronic acid and phosphate buffered saline (PBS) in the standard adhesion model involving the injury of abrasion and devascularization of both uterine horns of rabbits. Their treatment consisted of 15 ml of hyaluronic acid (2.5%, 8000

CPS) and tolmetin sodium (1 mg/ml) in PBS, administered intra-peritoneally via a syringe. Gross observations indicate that the occurrence of mild to severe adhesions within 72–96 hours after surgery occurred in 25% of those animals treated with HA-tolmetin sodium, whereas mild to severe adhesions were observed in 60% of untreated controls during the same time period.

In summary, developing appropriate and effective therapies for inhibiting inflammation and adhesion formation is still a major challenge. While NSAIDs have been shown to decrease the tissue inflammatory response and enhance fibrinolytic potential in peritoneal tissues previous studies have shown that these drugs need to be delivered to specifically targeted areas for several days to be effective. In turn, while hyaluronic acid has demonstrated potential as a drug carrier, the concentrations and molecular weights required for biological efficacy prohibit the practical use of this compound in an injectable form. Therefore, more effective strategies for the treatment of tissue trauma associated with adhesion formation are still needed.

SUMMARY OF THE INVENTION

The present invention is based on the discovery that novel compositions containing high molecular weight hyaluronic acid (HA), non-steroidal anti-inflammatory drug(s) (NSAIDs), and an excess of at least one organic salt of at least one divalent metal (organometallic salts), unexpectedly form a composition with a viscosity that is easily injectable, but which increases in viscosity at the site of injection to form a gel thereby resulting in prolonged residence time of the composition in the biological environment. A study of such a composition in an in vivo animal model indicates that these compositions demonstrate a 100% incidence of reduced adhesion formation over control specimens, and thus, are more efficacious in preventing adhesions than previously studied formulations.

Therefore, in one aspect, the invention features injectable therapeutic compositions containing hyaluronic acid, a non-steroidal anti-inflammatory drug, and at least one organic salt of at least one divalent metal selected from the group consisting of magnesium acetate, zinc acetate, calcium gluconate and ferrous gluconate. Preferably, the organic salt of the divalent metal is ferrous gluconate, which is also capable of acting as an anti-coagulant.

In preferred embodiments, the HA has a molecular weight of at least $1.0 \times 10^6$ Daltons; more preferably between $1.5 \times 10^6$ and $3 \times 10^6$ Daltons; even more preferably between $1.8 \times 10^6$ and $2.6 \times 10^6$ Daltons; and most preferably the molecular weight of the HA is between $2 \times 10^6$ and $2.5 \times 10^6$ Daltons. As used herein, the term "HA" means hyaluronic acid and any of its hyaluronate salts. Preferably, the HA used in the composition of the invention is sodium-hyaluronate.

The non-steroidal anti-inflammatory drug preferably contains free-carboxyl groups capable of interacting with the organic salt of a divalent metal. The NSAID can be in the form of a biologically acceptable salt (e.g., sodium), but preferably is in free acid form. Most preferably, the NSAID is chosen from group including tolmetin, ibuprofen, naproxen, peptides or mixtures thereof. Preferably, the peptide is cyclosporin. NSAIDs, as is well known in the art. are defined as compounds which decrease prostaglandin synthesis but do not affect arachidonic acid levels.

The organic salts of the compositions preferably contain a fatty acid component, e.g., acetic, gluconic and higher homologs thereof, and a divalent metal such as $Ca^{2+}$, $Mg^{2+}$, $Zn^{+2}$ or $Mg^{+2}$. Mixtures of organic salts may also be used.

Also in preferred embodiments, the concentration of HA in the composition varies between 10 to 25 mg/ml, and is preferably is between 15 to 20 mg/ml. The concentration of NSAID(s) is between a bout 0.5 to 3 mg/ml, and is preferably 1 to 2 mg/ml. The organometallic salt concentration is between 150–400 mg/ml, preferably between 150–250 mg/ml, and more preferably between about 170–200 mg/ml.

The viscosity of the composition is greater than 10 dl/g, but less than 18 dl/g, and more preferably is about 16 dl/g at 30° C. The ratio of HA to NSAID(s) is the composition is in the range between about 5 to 30 mg/ml, preferably about 10 to 25 mg/ml, and more preferably is between about 15 to 22 mg/ml. The ratio of the organic metal salt is in the range between about 15 to 4 mg/ml, preferably 12 to 6 mg/ml, and more preferably about 10 to 8 mg/ml. In one preferred embodiment, the therapeutic composition of the invention contains about 20 mg/ml hyaluronic acid, 200 mg/ml of divalent metal organic salt, and 1 mg/ml of cyclosporin A.

In another aspect, the invention features a method of inhibiting inflammation and adhesion formation in a mammal, preferably a human, by administering to the mammal a therapeutic composition containing hyaluronic acid (HA), a non-steroidal anti-inflammatory drug (NSAID), and an organic salt of a divalent metal in a dosage effective to inhibit inflammation and adhesion formation.

In various embodiments of this aspect of the invention, the method is used for the treatment of a mammal at risk of adhesion formation due to a medical condition which is associated with inflammation and scar formation. By the term "medical condition" as used herein is meant any trauma or disease of a bodily tissue which is associated with an increased inflammation of the tissue and the formation of permanent fibrous adhesions. The terms "fibrous adhesions", "adhesion formation" and the like, as used herein, refer to dense, fibrous scar tissue characterized by a grade of 3–5 as defined by the grading scale described by Rodgers et al. (1990, supra). Examples of diseases associated with the formation of fibrous adhesions include traumatic arthritis, osteoarthritis and bursitis. Examples of trauma include those caused by injury or surgical procedures.

In preferred embodiments, the method of the invention is used to treat a mammal at risk of developing adhesions due to a surgical procedure including but not limited to peritoneal, pericardial, obstetric, gynecology, neurological, ophthalmic, orthoscopic, orthopedic, plastic, reconstructive, prosthetic, muscle or tendon. In especially preferred embodiments, the method involves inhibiting adhesion formation between tendons and their sheaths during and after surgical procedures, e.g., in finger and knee joints.

In the method of the invention, the pharmaceutical composition of the invention is preferably administered locally to the site at risk of adhesion formation either during or alter trauma to the area (e.g., during or after a surgical procedure). Preferably, the composition is administered after the surgical procedure has been completed. In preferred embodiments, the method involves injection of the therapeutic composition using a 27–18 gauge needle, and more preferably using a 23–20 gauge needle. "Local administration," as used herein, refers to the contacting of a therapeutic composition in the immediate proximity of the tissue in the body where its therapeutic effect is desired.

Unless defined otherwise, all technical and scientific terms used herein have the same meaning as commonly understood by one of ordinary skill in the art to which this invention pertains. Although any method and materials similar or equivalent to those described herein can be used in the practice or testing of the present invention, the preferred methods and materials are now described. All publications mentioned herein are incorporated by reference. Unless mentioned otherwise, the techniques employed or contemplated herein are standard methodologies well known to one of ordinary skill in the art. The materials, methods and examples are illustrative only and are not intended to be limiting.

Other features and advantages of the invention will be apparent from the following detailed description and from the claims.

DETAILED DESCRIPTION OF THE INVENTION

Purified HA suitable for use in the therapeutic compositions of the invention can be obtained from a number of commercial sources (Genzyme Corp., Cambridge, Mass.) or prepared according to methods described in the art (See, for example, Balazs, U.S. Pat. No. 4,141,973). High molecular weight HA, i.e., greater than $1 \times 10^6$ Daltons is best suited for the compositions described herein. Molecular weights of HA can be determined by light scattering measurements as described in Yu et al., "Rheological Characteristics of Microbially Derived Sodium Hyaluronate", American Chemical Society Proceedings Series—Harnessing Biotechnology for the $21^{st}$ Century, M. R. Ladisch and R. Bose eds., pp. 80–84, 1992.

NSAIDs and organometallic salts appropriate for use in the therapeutic compositions of the invention are also available from a number of commercial sources known to those skilled in the art and described herein.

The major therapeutic components of the compositions of the invention, the HA, NSAIDs and organometallic salt can be combined as described herein or by methods well known to the skilled artisan. Typically, the organometallic salt will be in a concentration such that the ionic composition of the salt exceeds the free carboxyl groups of the HA and drug. The concentration of the drug will depend on the condition to be treated, but will typically be in the range found to be effective for local, continuous delivery systems (e.g., see Rodgers, 1990, supra). The particular dosage of NSAID used in the composition will be influenced by a number of factors including the type and extent of the trauma, and overall health and status of the particular patient. For most applications, the dose of the drug will range between 0.5 to 3 grams per milliliter of the formulation.

The amount of HA used in the formulation will generally be in an amount which produces a formulation with an initial viscosity outside the biological environment that is greater than 10 dl/g at 30° C., but can be optimized to suit the particular application. Viscosity of the pharmaceutical composition of the invention can be determined as described herein, or by methods well known is by use of a Brookfield cone and plate viscometer using the lowest shear rate that yield results greater than 10% full scale.

Compositions for administration according to the method of the invention comprise a combination of HA, NSAID and an organic salt of a divalent metal dissolved or dispersed in an acceptable carrier, preferably an aqueous carrier. A variety of aqueous carriers may be used, e.g., water, buffered 0.9% saline, and the like. The compositions may also contain pharmaceutically acceptable auxiliary substances as required to approximate physiological conditions, such as pH adjusting and buffering agents, tonicity adjusting agents, wetting agents and the like.

Injection of the therapeutic compositions according to the method of the invention can be accomplished by means generally known to those skilled in the art. Generally, the amount of the therapeutic composition used will depend on the specific site of the body to be treated. For some applications a single administration will often be sufficient to inhibit inflammation and adhesion formation at the desired site. However, where continued or chronic pain is experienced (e.g., in joint inflammation), repeated applications may be used without adverse effect. Local administration is preferred via a syringe according to well established techniques, e.g., using a needle having a gauge size capable of effectively extruding the formulation while minimizing the invasiveness of the procedure.

Generally, surgical procedures, according to the method of the invention employ proper techniques for minimizing the risk of adhesion prevention (see, for example, Stangel et al. 1984. supra). The basic keys to good surgical technique include limiting trauma, ischemia, foreign body interactions, hemorrhage, raw surfaces and infection. These techniques are applicable to all types of surgical procedures and they significantly increase the potential for successful healing and recovery.

Surgical trauma can be limited by handling tissues as little as possible and using appropriate instrumentation. Ischemia, the most potent stimulus in adhesion formation, should be avoided by maintaining the vasculature of the tissue. Foreign bodies such as glove powder, lint, gauze particles, and suture remnants should be carefully removed from the surgical field. These various particles will initiate granulomatous reactions and trigger adhesion formation if left behind in vivo (Levinson and Swolin, *Clin. Obstet. Gynecol.* 23:1212, 1980).

It is also important to maintain hemostasis, thereby limiting the amount of blood at the site and decreasing one of the main sources of fibrin. Irrigation should be used as opposed to swabbing with gauze to prevent abrasion of the tissue surfaces and the resultant cell damage. Finally, aseptic techniques and prophylactic antibiotic use are important in reducing the risk of infection post-surgically and limiting complications that can lead to adhesion formation.

EXAMPLE

In the following study, compositions which contained sodium hyaluronate gels and different combinations of tolmetin sodium, naproxen sodium, and calcium acetate were evaluated in a tendon adhesion model. Tolmetin sodium and naproxen sodium were selected based on their reported effectiveness in reducing inflammation in previous studies. Calcium acetate was chosen as a potential ionic cross-linking agent based on the initial hypothesis that the calcium ions would preferentially exchange with two sodium ions in the HA chains or the drug molecules in solution, thereby creating an ionic crosslink between the drugs and HA or between the HA molecules.

Materials and Methods

Implants

Five different gel compositions were designed to study the individual effects of hyaluronic acid (HA) (Genzyme Corp., Cambridge, Mass.), tolmetin sodium (R. W. Johnson Pharmaceutical Research Institute, Spring House, Pa.), naproxen sodium (Sigma Chemical Co., St. Lois, Mo.), and calcium acetate (J. T. Baker, Inc., Phillipsburg, N.J.) on adhesion formation. All of the sodium hyaluronate used in the experimental study was obtained from Lot C3040 (Genzyme Corp.), and had a molecular weight of $2.3 \times 10^6$ Dalton. A base concentration of 2% w/v HA in phosphate buffered saline (H=7.44) was used for each gel. Both the tolmetin sodium and naproxen sodium were dosed in concentrations of 1 mg/ml. While the chosen concentration of calcium acetate was 0.216 g/ml. The individual composition of each gel was as follows:

1. HA: 20 mg/ml;
2. HA: 20 mg/ml, tolmetin sodium 1 mg/ml;
3. HA: 20 mg/ml, naproxen sodium 1 mg/ml;
4. HA: 20 mg/ml, calcium acetate: 0.216 g/ml; and
5. HA: 20 mg/ml, naproxen sodium 1 mg/ml, calcium acetate: 0.216 g/ml.

This concentration of calcium acetate was calculated to allow for maximum ionic cross-linking between the carboxyl groups of the HA backbone and those in naproxen sodium. This concentration is also reasonably within the solubility range of calcium acetate.

Because hyaluronic acid is highly susceptible to bacterial degradation, aseptic techniques were used throughout the gel preparation phase of this study. All work with HA was conducted under a laminar flow hood (Labcona Purifier Class 11 Safety Cabinet, Labcona Corp., Kansas City, Mo.) which was regularly sterilized with an internal UV light source. A Mettler AE 100 analytical balance (Mettler Instrument Corp., Highstown, N.J.) was thoroughly cleaned with 70% ethanol wipes and moved under the hood. It was then leveled and balanced, and exposed to UV light for 24 hours. This scale was used to measure the components of each gel.

Measuring spatulas, magnetic stirbars, and 20 ml disposable scintillation vials (Kimble Glass, Inc., Vineland, N.J.) were placed in sterilization bags (Baxter Healthcare Corp., Deerfield, Ill.) and were steam sterilized in an autoclave (American Sterilizer, Erie, Pa.). All glassware that was used was acid washed, and every article was thoroughly wiped with 70% ethanol before entering the hood.

Twenty 0.200 gram aliquots of HA were measured and stored in scintillation vials at 4° C. A stock solution of phosphate buffered saline (PBS, ph=7.44) was prepared and filter sterilized using a disposable bottle top filter with a 0.22 $\mu$m cellulose acetate membrane (Corning Glass Workings, Corning, N.Y.). Two separate stock solutions of tolmetin sodium (1 mg/ml) and naproxen sodium (1 mg/ml) in PBS were made and filter sterilized as described above. A fourth stock solution of naproxen sodium (1 mg/ml) and calcium acetate (0.216 g/ml) in PBS was also prepared. All solutions were stored at 4° C.

Gels were made up to 24 hours prior to surgical use by adding 10 ml of the appropriate stock solution to one aliquot of HA. A sterile magnetic stirbar was added to each vial and the vials were sealed prior to removal from the sterilization hood. Following manual agitation, each gel as sonicated (Branson 1200, Branson Cleaning Co., Shelton, Conn.) for 1 minute. The vials were then placed on a Corning Stirrer/Hotplate (Corning Glass Works, Corning, N.Y.) and stirred on the "high-scale" for 4 hours at room temperature. Following homogenous mixing, the gels were once again stored until 4° C. until surgery.

Viscosity Measurements

Solutions were prepared with a concentration of 0.1% w/v HA and the appropriate dilutions of the other components for solution viscosity testing. Initial tests were run in a 3° C. constant temperature water bath, using a 100 capillary viscometer (Ostawald type). Five measurements were taken for each individual solution to determine the inherent viscosity ($n_{inh}$). The solutions were then stored at 4° C. for 24 hours.

A second set of viscosity measurements were recorded 24 hours after solution preparation to determine the effect of storage prior to surgery. These tests were also run at a constant temperature of 30° C., with five measurements recorded for each solution.

Animals

The white leghorn chicken was chosen as the animal model. The anatomical arrangement of tendons in the foot of the chicken is very similar to that of the human hand (Craver et al., *Surg.* 64(2):437, 1968) making this species clinically relevant. The surgical model we have adopted is based on one designated by Daley et al. (*Proc. Orthop. Res. Soc. Ann. Mtg.* 38:1–3, 1992) for the specific application of testing biomaterials for adhesion prevention.

Chickens were also chosen due to their vulnerability, cost effectiveness, and ease of maintenance. Fifty-six female, adult, white leghorns were obtained from Morgan Poultry Farm (Clemson University, Clemson, S.C.). They were housed two birds per cage by Clemson Research Services at either Jordon Hall or the Poole Agriculture and Sciences Building for one week prior to surgery. The birds weighed between 1.03 kg and 2.02 kg per-operatively and between 0.92 and 2.24 kg at necropsy.

Surgical Protocol

Each animal was given Buprenorphine (0.03 mg/kg, IM) up to 2 hours before surgery as a premedication. Anesthesia was induced with 2–3% Forane™ in oxygen (2 l/min) administered through a fitted mask. Once induced, the birds were intubated with a 3 mm ID endotracheal tube and maintained using 2–3% Forane™ in oxygen (2 l/min). Respiratory rate and capillary refill time were used to monitor anesthetic depth and oxygen perfusion.

A major concern in avian surgery is body heat loss. Therefore all birds were placed on a water blanket perioperatively and wrapped in towels post-operatively. Also, the operative foot was prepped with alternating solutions of Nolvasan Surgical Scrub (Aveco, Co., Inc., Fort Dodge, Iowa) and sterile 0.9% Sodium Chloride Irrigation USP (Baxter Healthcare Corp., Deerfield, Ill.), to prevent evaporation cooling that often occurs with alcohol.

(a) Pilot Study

Under tourniquet control, a 2.5 cm incision was made in the plantar aspect of the long central digit of the chicken's left foot. The tendon sheath, or peritenon, was incised exposing the flexor sublimis tendon. The sublimis was retraced along with the peritenon to expose the flexor profundus tendon. A 50% tenotomy was made in the flexor profundus and sutured with a modified Kesler stitch using 3-0 Ethibond™ suture (Ethicon, Inc., Somerville, N.J.).

The peritenon was closed with a simple continuous stitch using 3-o Ethibond™. A gauze dressing was applied to the foot covering the incision. Padding and a fiberglass cast (Carapace, Inc., Tulsa, Okla.) were applied with the toes in hyperextension and the foot in flexion. This type of immobilization relieves tension at the repair site in the tendon and allows the bird to walk easily. Co-Flex wrap (Andover Coated Products, Inc., Marblehead, Mass.) was applied to each cast to minimize contamination, and this wrap was changed regularly.

(b) Experimental Study

In order to test the effectiveness of each gel, animals were randomly assigned to one of six groups, with eight animals per group. One group served as the control, while the other five groups each received a different gel treatment.

The surgical procedure was slightly modified for the experimental study by changing the sutures that were used. The flexor profundus tendon and the tendon sheath were sutured with 3-0 Chromic (Ethicon, Inc., Somerville, N.H.). Following closure of the sheath, 0.2 ml of each gel was delivered to the intra-sheath region by a tuberculin syringe. The skin was closed with 3-0 Silk (Ethicon, Inc., Somerville, N.H.). All other aspects of the surgical procedure remained the same throughout the in vivo study. There were no notable modifications or complications in any aspect of anesthesia or surgery. All animals maintained respiratory rates and anesthetic depths within normal ranges. The surgical procedure lasted approximately thirty to forty minutes per animal.

Recovery from inhalation of anesthesia was quite rapid in birds (approximately 3–5 minutes). Initial recovery from anesthesia was rapid and without complication for all of the animals in the study. During this time period each animal was given 15 cc of Lactated Ringer's Injection USP (McGaw, Inc., Irvine, Calif.) subcutaneously to maintain proper hydration. Each bird was alert and on its feet within ten to fifteen minutes. In general, the chickens exhibited normal behavior from immediately following surgery until euthanasia two weeks later. This included regular eating habits, alert and active behavior, full weight bearing on each foot, no pronounced limping, no need for additional analgesics, and no significant loss of body weight (<<20% of pro-surgery weight).

All birds were returned to their pre-operative housing within a few hours of surgery. Body weight, appetite, behavior and weight bearing on the casted foot was closely monitored to assess post-operative health. Buprenorphine (0.03 mg/kg, IM) was given 12 hours post-operatively and subsequently every eight hours if needed for pain. A humane endpoint was set at 20% loss of body weight.

Four of the fifty-six animals had to be removed from the study due to post-operative complications. Three of these birds were euthanized prior to the two week time period. Each one developed a pronounced limp within several days of surgery. They were treated with Buprenex (0.03 mg/kg, IM, every eight hours) but did not respond to the analgesic treatment. These birds were lethargic and reluctant to bear weight on their immobilized foot. Additionally, they had depressed eating habits accompanied by significant weight loss. None of these birds reached the humane endpoint of 20% body weight loss; however, they were euthanized due to signs of unalleviated pain.

Upon examination, these three specimens did not show any gross signs of infection. There was no evidence of swelling, redness, exudate, or poor healing. There were some signs of light bruising on the distal ends of several of the toes involved, possibly caused by the cast itself. If the cast was applied too tightly, it may have caused bruising and discomfort. This is a plausible explanation for the limping observed in these birds. It should also be noted that each of the affected animals came from different experimental groups showing no bias toward a specific implant.

The fourth bird was not prematurely euthanized; however, the flexor profundus tendon was completely ruptured at the suture site when the gross evaluation was performed. This was not consistent with the surgical model and was therefore eliminated. The cause of this rupture is unknown.

Euthanasia and Specimen Retrieval

After 2–4 weeks for the animals in the pilot study, and 2 weeks for those in the experimental study, each chicken was terminated with carbon dioxide in a pre-charged chamber. The left foot of each bird was removed above the cast and the casts were cut using a Richard Oscillating Saw (Richards Manufacturing Co., Memphis, Tenn.). Casts, padding, and gauze were discarded and the feet were labeled and stored below 0° C. until gross evaluation could be conducted.

X-Ray Analysis

A radio-opaque gel of 2% w/v HA was formed in 50% PBS and 50% Hypaque sodium (Sanofi Winthrop Pharmaceuticals, New York, N.Y.). Initial x-rays were taken of a cadaver foot as a baseline for comparison. The gel was then applied to four cadaver feet using the described surgical procedures. Anteroposterior and mediolateral x-rays were taken of each foot to verify the placement of the gel during its surgical application.

Gross Evaluation

All specimens were grossly dissected in groups of at least twelve for comparative purposes. The feet were thawed and observations of inflammation, and the skin closure were noted. Skin sutures were removed and the toe was dissected through the original incision. Subcutaneous inflammation and adhesion formation was recorded. The peritenon grading scale (Table I) was used to evaluate the extent and severity of adhesion formation within the intra-sheath region.

TABLE I

Qualitative Grading Scale[a]

| Grade | Evaluation |
|---|---|
| 1 | No Adhesion |
| 2 | Filmy (separable) |
| 3 | Mild (not separable) |
| 4 | Moderate (35–60% of area) |
| 5 | Severe (greater than 60% of area) |

[a](Rodgers et al., 1990 supra).

More specifically, for the gross evaluation all specimens were categorized based on the maximum severity of the adhesions present. For example, if a particular specimen exhibited primarily thin, filmy adhesions but had one small band of non-separable fibrous tissue, it was classified as a grade 3 rather than grade 2, its predominant type.

Each grade division on the scale was associated with a set of specific gross characteristics. Grade 5 specimens were characterized by dense, fibrous adhesions covering virtually the entire surgical field. They involved the profundus and sublimis tendons, along with the tendon sheath and underlying bone. There were adhesions present between the tendons and form the tendons to the surrounding structures.

Grade 4 specimens were similar to those in grade 5; however, the scarring was slightly less extensive. The adhesions were still characterized by dense, fibrous scar tissue but there was less involvement at the profundus tendon. Adhesions were most predominant between the flexor sublimis and the tendon sheath and between the two tendons.

The specimens that were classified as grade 3 were quite different from the previous two groups. These adhesions were very predominant between the tendon sheath and the flexor sublimis. In some cases these two tissue structures were firmly adherent throughout the length of the surgical field. In other cases the majority of the adhesions between the sheath and sublimis were filmy with the presence of non-separable fibrous bands in one or two localized areas. There was almost no involvement of the flexor profundus tendon. Any adhesions to this tendon were minimal and filmy in nature.

Grade 2 adhesions are filmy and easily separable as defined by the grading scale (Rodgers et al. 1990, supra). These were easily distinguishable from the more severe grades 3–5 because there were no fibrous bands of scar tissue present between adjacent tissue structures. Grade 2 specimens were characterized by thin, wispy adhesions present between the tendon sheath and the flexor sublimis. There was virtually no involvement of the flexor profundus and this tendon was able to glide freely in both directions upon manipulation. The adhesions that were present between the sheath and the sublimis were easily dissectable and the tissue structures separated from each other with very little applied force.

A grade of 1 in the chosen scale is representative of no adhesion formation. Even under ideal surgical conditions, there will be some degree of scar tissue formation. Scarring was visible in the subcutaneous tissue of all specimens; however, it was proportional to the overall quality of healing and adhesion formation. Ideally, specimens that are classified as grade 1 should appear identical to their pre-operative condition. This was not the case with any of the animals evaluated in this study. However, a number of specimens were judged to be significantly different from the typical grade 2 category. These specimens showed a very limited incidence of extremely filmy adhesions between the sheath and flexor sublimis. The tissue structures separated immediately upon dissection of the tendon sheath. Ultimately, these specimens were assigned a grade of 1.5 for the purpose of data evaluation. While they did not meet the stringent criteria established for grade 1, they were significantly different from grade 2 adhesions in their extent and quality.

Following gross evaluation, specimens were disarticulated at the metacarpophalangeal joint and placed in containers of 10% neutral buffered formalin for histological preparation.

Histological Preparation

Fourteen specimens were selected and submitted for histological processing and evaluation. They were chosen based on their gross evaluation grades and their experimental groups (Table II). Specimens were trimmed grossly of any excess bone, skin, etc. and placed in tissue cassettes. They were processed in the Tissue Tek V.I.P.™ Tissue Processor (Miles Scientific, Miles, Inc., Mishawaka, Ind.) using a modified version of program zero (Table III). following processing the specimens were removed from the tissue processor and blotted dried to remove excess xylene.

TABLE II

Specimens Submitted for Histological Evaluation

| Specimen No. | Test Group[a] | Gross Grade |
|---|---|---|
| 94-C-51 | CONTROL | 5 |
| 94-C-53 | CONTROL | 4 |
| 94-C-56 | CONTROL | 5 |

TABLE II-continued

Specimens Submitted for Histological Evaluation

| Specimen No. | Test Group[a] | Gross Grade |
|---|---|---|
| 94-C-61 | HA | 4 |
| 94-C-65 | HA | 3 |
| 94-C-70 | HA + TS | 3 |
| 94-C-71 | HA + TS | 2 |
| 94-C-75 | HA + NS | 2 |
| 94-C-78 | HA + NS | 3 |
| 94-C-80 | HA + NS | 1.5 |
| 94-C-82 | HA + CA | 3 |
| 94-C-92 | HA + CA | 2 |
| 94-C-93 | HA + CA + NS | 2 |
| 94-C-96 | HA + CA + NS | 1.5 |

[a]ts: tolmetin sodium, NS: naproxen sodium, CA: calcium acetate

TABLE III

Modified Program Zero

| Solution[a] | Time | P/V[b,c] | Temperature |
|---|---|---|---|
| 10% NBF | 20 min. | Y | 40° C. |
| 10% NBF | 1 hr. | Y | 40° C. |
| 70% EtOH | 30 min. | Y | 40° C. |
| 80% EtOH | 30 min. | Y | 40° C. |
| 95% EtOH | 45 min. | Y | 40° C. |
| 95% EtOH | 45 min. | Y | 40° C. |
| 100% EtOH | 45 min. | Y | 40° C. |
| 100% EtOH | 45 min. | Y | 40° C. |
| Hemo-De | 40 min. | Y | 35° C. |
| Xylene | 1 hr. | N | 35° C. |

[a]EtOH: ethanol; [b]P/v: Pressure/Vacuum; [c]Y=yes, N=no

The selected specimens were infiltrated in a series of graded solutions of TECHNOVIT 7100 (Delaware Diamond Knives, Wilmington, Del.), a glycomethacrylate embedding medium. All diluted solutions were mixed with 100% ethanol to yield the appropriate concentrations. The tissue cassettes were placed in 50% TECHNOVIT 7100 for 48 hours. They were then transferred to 75% TECHNOVIT 7100 for another 48 hours. Finally, the cassettes were infiltrated in 100% TECHNOVIT 7100 for 72 hours. All of the infiltration mediums were agitated under a vacuum and protected from light.

Once infiltrated, each specimen was embedded in a solution of 100% TECHNOVIT 7100 and Hardener II, mixed in a 15:5 ratio, as specified for large specimens in the package insert. Specimens were arranged in disposable plastic molds (4.5 cm×2.7 cm×2.0 cm) and covered with 15 ml of the embedding solution. They were placed in a desiccator and polymerized under vacuum for 24 hours.

Following polymerization, the tissue blocks were very rubbery. Normally the polymerized blocks are a hard, solid mass. These blocks were not of the appropriate hardness to cut on the Polycut E Microtome (Reichert-Jung, Reichert Scientific Instruments, Buffalo, N.Y.). The blocks were subjected to heat, cold, and vacuum conditions in attempts for further polymerization. These unsuccessful attempts were discontinued 48 hours later, and specimens were recovered and re-embedded.

Slides were stained with Hematoxylin and Eosin, Masson's Trichrome (Poly Scientific Corp., Bay Shore, N.Y.), and a modified Trichrome for GMA embedded tissues (Osheroff and Ruffing, *J. Histotech.* 8:92, 1985). The specific staining procedures are listed in appendix a.

Histological Evaluation

The histological evaluation was done subjectively and qualitatively. Observations focused on the amount of granulation tissue present, the presence of inflammatory cells, the relative thickness of granulation tissue and adhesion formation around the tendons, and location of post-surgical adhesions. Due to the difficulty in tissue processing, the quality of slides was not sufficient to perform a detailed histological analysis. However, general observations were made and correlated with the results of the gross evaluation.

Statistical Analysis

Microsoft Excel (version 4.0a) was used to perform analysis of variance (ANOVA) and student t-tests to evaluate the results of the gel viscosity tests and the in vivo gross evaluation. P-values less than 0.05 were considered significant differences, while p-values less than 0.01 were considered highly significant.

Results and Discussion

Gel Characterization

All of the gels were prepared as described above without modification. Solution viscosity tests were used to calculate inherent viscosity ($\eta_{inh}$), verify the stability of the gel compositions during storage, and establish a relationship between gel viscosity and effectiveness in vivo. Hyaluronic acid is an absorbable polymer susceptible to bacterial degradation. Degradation of the polymer chains results in a decrease in molecular weight. The inherent viscosity of a polymer is proportional to its molecular weight. Thus, significant degradation of the polymer would result in a substantial decrease in inherent viscosity.

The inherent viscosity of each gel was determined immediately following preparation (t=0 hr) and twenty-four hours later (t=24 hr) to determine the effect of storage at 4° C. None of the gels were stored for more than 24 hours prior to surgical implantation, therefore their stability was not investigated beyond this time period. The results of the solution viscosity tests arc listed in Table IV. All data is shown as inherent viscosity in the units of deciliters per gram (dl/g). Each data point is the average of five repetitions of one solution.

for the experimental study. X-rays of the feet showed that the gels are concentrated and confined to a localized space between the distal half of the proximal phalanx and the proximal half of the medial phalanx. This is consistent with the location of the surgical field. Mediolateral views of the specimens illustrate the presence of gel in the soft tissues of the toe. This confirms that the implants were properly delivered to the targeted area in this surgical model.

Gross Evaluation

The in vivo research involved a pilot study and a subsequent experimental study to evaluate the effectiveness of each gel composition. The pilot study was primarily used to become familiar with the surgical model and to evaluate the consistency of results. The grades of from gross evaluation of the animals in the initial pilot study ranged from 2 to 4, with little variation between the two and four week time period. These results were judged to be insufficient in terms of severity for the control portion of the study.

The objective was to elicit a response in the 4 to 5 range from the surgical model alone. The sutures used in the pilot study were changed from Ethibond™ to Chromic and Silk in order to produce a more severe response. This was a successful modification and the control group had a mean adhesion score of 4.875/5. All of the grade 5 adhesions reported throughout the study were confined to the control group where they represented 87.5% of the data of this set. Based on these results, the animal model was judged to be both effective and consistent in producing severe tendon adhesions. Its effectiveness can be attributed to the combination of tendon sheath incisions, tendon injury and suturing, and full immobilization (Matthews and Richards, J. Bone and Joint Surg. 58-b(2):230, 1976).

Figure 1:
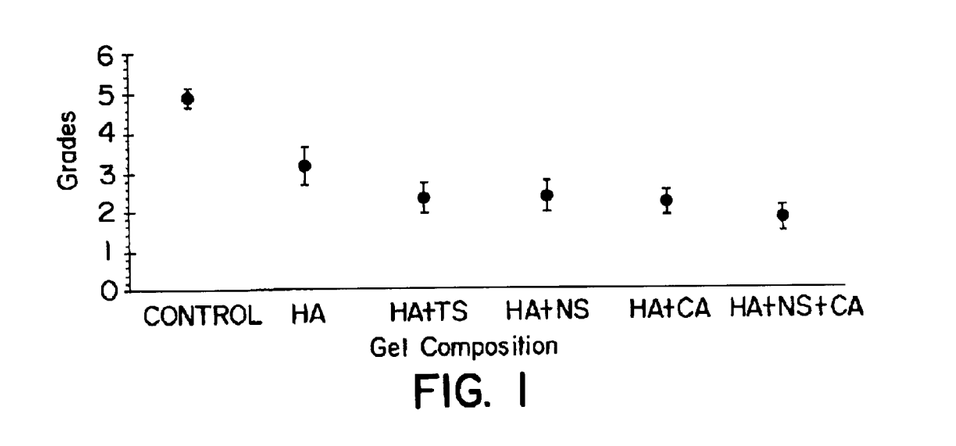
FIG. 1 is a graph representing the correlation between gross evaluation grades and gel composition.

The results from the experimental evaluation of each gel composition are shown in FIG. 1. This graph represents the data as a 95% confidence interval about the mean for each data set. ANOVA was performed on the data with the null hypothesis that all of the group means were equal. This hypothesis was rejected and the data was further evaluated for specific differences.

Results from the statistical analysis strongly supported the fact that all of the gel treatments were significantly effective

TABLE IV

Inherent Viscosity Results

| Time (hr) | HA (dl/g) | HA + NS (dl/g) | HA + TS (dl/g) | HA + CA (dl/g) | HA + CA + NS (dl/g) | Average (dl/g) |
| --- | --- | --- | --- | --- | --- | --- |
| 0 | 18.91 | 19.50 | 19.48 | 16.10 | 16.21 | 18.04 |
| 24 | 18.74 | 19.64 | 19.58 | 16.13 | 16.05 | 18.02 |

Although there are slight fluctuations in the inherent viscosities of the different gels at 0 and 24 hours, none of these differences are statistically significant. There is no specific trend in the data. Analysis of variance (ANOVA) does not indicate any significant difference in the overall average $\eta_{inh}$ between the two time periods (p+0.955). These results confirm the stability of each gel composition during storage prior to surgery.

Necropsy

In general, the tissues of the involved feet appeared healthy and normal. The skin incisions were completely healed and there were no gross signs of infection. The necropsy results indicated that all of the implanted materials were sufficiently sterile.

x-Ray Analysis

Samples of radio-opaque HA gel were injected into four different cadaver feet using the surgical procedure described in limiting adhesion formation as compared to the control group. The least significant difference was between the simple HA gel and the control, which yielded a p-value much less than 0.01. In addition, all medicated or "cross-linked" treatments (those with NSAIDs and/or calcium acetate added) were significantly more effective than the HA alone (Least significant difference: p<0.05). There was no statistical difference between the effectiveness of the NSAIDs tolmetin sodium and naproxen sodium.

The addition of calcium acetate to the HA gel significantly improved its effectiveness (p<0.01). Calcium acetate also had a significant positive effect when it was added to the HA-naproxen sodium gel. The mean score of the HA+CA+NS gel was significantly lower than both the HA+NS score (p<0.05) and the HA+CA score (p<0.05).

It is apparent that the addition of NSAIDS and calcium acetate, as a "cross-linking" agent, has a profound effect on the in vivo performance of the gels in this animal model. It was hypothesized that this effect would be partially due to the anti-inflammatory properties of the two drugs and also to the expected increase in viscosity from cross-linking the gels. However, the inherent viscosities of the gels with the calcium acetate were substantially lower than expected prior to their administration. There was actually a decrease in $\eta_{inh}$ between the simple HA and HA-NSAID gels and those gels crosslinked with calcium acetate.

Hyaluronic acid has a high inherent viscosity because it is an extremely large molecule (MW: $2.3 \times 10^6$ Dalton). The increase in inherent viscosity between the HA gels and the HA-NSAID gels is due to the incorporation of the relatively small drug molecules in the HA gel matrix, although there is no stimulus for chemical interaction between these molecules. Cross linking increases the molecular weight of the polymer, and thus was expected to increase the viscosity. However, unexpectedly, "cross-linking" with calcium acetate did not produce an initial increase in viscosity, but rather resulted in a lowering of the viscosity of the composition containing all three components.

Figure 2:
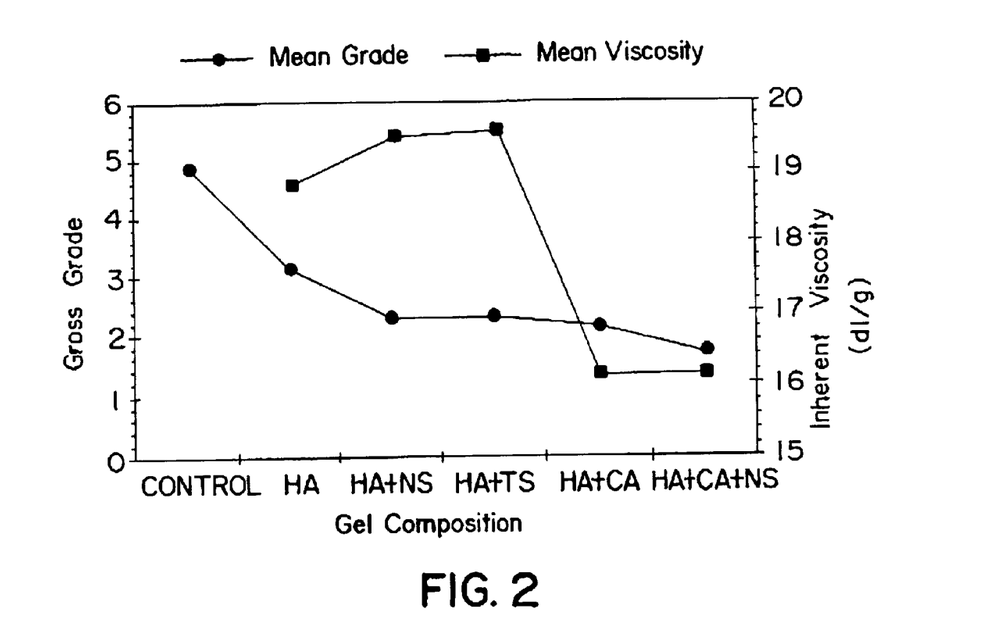
FIG. 2 is a graph that illustrates the relationship between gel composition, inherent viscosity and in vivo effectiveness.

FIG. 2 illustrates the relationship between gel composition, inherent viscosity, and in vivo effectiveness. Hypothetically, gels containing the combination of HA and NSAIDS with the highest viscosity should demonstrate the optimal in vivo performance. In contrast to the expected result, the HA+CA+NS gel, which demonstrated a significantly lower viscosity was the most effective in preventing adhesion formation.

One explanation for this unexpected observation of the relationship between inherent viscosity and efficacy is that the addition of calcium acetate in a closed system such as a preparation vial or an Oswald viscometer does not affect the molecular volume of the hyaluronic acid, but rather changes the ionic concentration of the gel resulting in an overall lower inherent viscosity. When these gels are then placed in an open system, such as the in vivo environment, ion exchange occurs and the byproduct of this reaction rapidly diffuses out of the hyaluronic acid matrix. In this case, the reaction byproduct is sodium acetate, and this in situ ionic cross linking leaves a higher viscosity gel at the surgical site. This would account for the effectiveness of the HA+CA and HA+CA+NS systems. The increased viscosity upon application yields a longer in vivo residence time for these compositions.

Histological Evaluation

The quality of the histological slides was only average due to the difficulties encountered in processing and embedding the tissue specimens. The procedure that was used to salvage and re-embedded the tissues resulted in blocks of appropriate harness for cutting on the microtome. However, when sections were cut from the blocks there was a notable difference in consistency of the polymeric embedding medium within the tissue as opposed to outside the tissue. Consequently, the tissues did not cut as well as expected. The medium was too soft to prevent shattering of the bone although this did not affect the evaluation. There was a significant amount of tearing and wrinkling in tissue sections. The longitudinal sections were most adversely affected because of the larger tissue surface area involved in cutting the sections.

Another difficulty in the histological evaluation was encountered in staining the slides. Hematoxylin and eosin stains were successful; however, the Masson's trichrome and the modified trichrome procedures yielded uneven staining patterns. Trichrome normally stains nuclei black, and cytoplasm, keratin, muscle fibers and intracellular fibers red; and collagen blue. Both of the procedures used in his study resulted in an uneven, somewhat random distribution of red a blue stain. This complication made it impossible to evaluate these slides in terms of collagen production. Therefore, and overall qualitative approach was taken in evaluating the histological slides. There were no notable differences in the characteristics of specimens from different treatment groups that were assigned to the same gross grade. Observations were thus made based on the amount of tissue in the intr-sheath space, the presence and location of adhesions, and the overall cellular response. These observations were then correlated with the grades from the gross evaluation.

The intra-sheath space of grade 5 specimens was filled with fibrous connective tissue indicative of dense adhesions. This tissue was very cellular, but notably avascular. Macrophages and fibroblasts were the predominant cellular components; however, eosinophils. giant cells, and plasma cells were also present. Additionally, a thick fibrous tissue capsule was observed around the circumference of each tendon. Adhesions were present between the tendons and from the tendons to the surfaces of the sheath and the bone.

Grade 4 specimens also exhibited a tissue response indicative of adhesion formation: however, to a lesser degree than grade 5 specimens. The presence of fibrous tissue was more predominant at the periphery of the tendons. Adhesions were present between the tendons and from the tendons to the sheath. The scar tissue present was less cellular in comparison to the grade 5 specimens, with macrophages and fibroblasts being the predominant cell type.

The amount of fibrous scar tissue decreased with each improvement in gross grades. Grade 3 specimens displayed little evidence of fibrous scar tissue around the profundus tendon; however, there were dense adhesions between the sublimis tendon and the sheath. Grade 2 specimens showed scant evidence of fibrous tissue around the profundus and a few areas of limited contact between the sheath and the sublimis. There were no signs of chronic inflammatory cells in any of these specimens. Unfortunately, the grade 1.5 specimens were longitudinal sections and their poor quality made it impossible to evaluate their histological characteristics.

Clinical Relevance

Ultimately the goal in post-surgical tendon adhesion prevention is to restore the functional performance of the affected digit. Dense, fibrous, non-separable adhesions restrict the gliding function of the flexor tendons. But filmy, separable adhesions are much more likely to undergo significant remodeling in the clinical setting with treatments such as physical therapy. These types of adhesions (categorized as grade 2 or less in this study) take much less force to break, and usually never present any significant functional impairment to the patient.

Therefore, it is interesting to relate this clinical perspective to the results of this animal study. Exactly two-thirds of all of the treaded specimens exhibited adhesions of grade 2 or less. The incidence of adhesions less than or equal to grade 2 was 82.76% in all of the medicated and/or crosslinked treatment groups. Most surprisingly however, 100% of the animals in the HA+CA+NS treatment group had scores of 2 or less. The success of these materials in this animal study of severe trauma certainly indicates the efficacy of these combinations in clinical adhesion prevention.

Without being bound by any one theory, according to the results of the study described herein, the excess organometallic salt concentration in the compositions of the invention appears to promote intr- and/or inter-molecular ion-binding of the HA molecules leading to substantial decrease in the polymer hydrodynamic volume and, hence, viscosity. Once injection of the composition into the biological environment within a constrained space occurs, there is an exchange of the metal. Ions with body fluids which produces an increase in the viscosity of the formulation to a gel form, and thereby provides an initial high coverage of the traumatized space. Further, due to the low pKa value of the typical NSAID, the solubility of the drug is decreased upon interacting with the divalent ion. This leads to minimized initial drug burst and a prolonged release period. Thus, the compositions of the invention are a significant improvement over those previously investigated became the biological efficacy of the components are maximized.

From the above description, one skilled in the art can easily ascertain the essential characteristics of the present invention, and without departing from the spirit and scope thereof, can make various changes and modifications of the invention to adapt it to various usages and conditions. For example, the compositions of the method may also be useful for the local delivery of other bioactive compounds including peptides and proteins, e.g., intravitreally.

What is claimed is:

1. A therapeutic composition for use in inhibiting tissue inflammation and adhesion formation in a mammal, said composition comprising hyaluronic acid, a non-steroidal anti-inflammatory agent, and at least one organic salt of at least one divalent metal selected from the group consisting of magnesium actate, zinc acetate, calcium gluconate and ferrous gluconate.

2. The therapeutic composition of claim 1 wherein the molecular weight of the HA is at least $1.0 \times 10^6$ Daltons.

3. The therapeutic composition of claim 1 wherein the non-steroidal anti-inflammatory agent is selected from the group consisting of tolmetin, ibuprofen, naproxen and peptides.

4. The therapeutic composition of claim 1 wherein the non-steroidal anti-inflammatory agent is a peptide.

5. The therapeutic composition of claim 4 wherein the peptide is cyclosporin A.

6. The therapeutic composition of claim 1 wherein the organic salt of a divalent metal is magnesium acetate.

7. The therapeutic composition of claim 1 wherein the organic salt of a divalant metal is zinc acetate.

8. The therapeutic composition of claim 1 wherein the organic salt of a divalant metal is calcium gluconate.

9. The therapeutic composition of claim 1 wherein the organic salt of a divalant metal is ferrous gluconate.

10. The therapeutic composition of claim 1 wherein the viscosity of the composition is less than 18 dl/g.

11. A therapeutic composition for use in inhibiting tissue inflammation and adhesion formation in a mammal, said composition comprising hyaluronic acid, cyclosporin A and at least one organic salt of at least one divalent metal selected from the group consisting of magnesium acetate, zinc acetate, calcium gluconate and ferrous gluconate.

12. The therapeutic composition of claim 11 wherein the organic salt of a divalent metal is ferrous gluconate.

13. A method of inhibiting or mediating tissue inflammation in mammal tissue, said method comprising administering to said mammal a therapeutic composition comprising hyaluronic acid, a non-steroidal anti-inflammatory agent, and at least one organic salt of at least one divalent metal in a dosage effective to inhibit or mediate local inflammation and adhesion formation in said tissue, wherein said organic salt of a divalent metal is selected from the group consisting of magnesium acetate, zinc acetate, calcium gluconate and ferrous gluconate.

14. The method of claim 13 wherein said mammal is at risk of tissue adhesion formation as a result of tissue injury.

15. The method of claim 13 wherein said mammal is at risk of tissue adhesion formation which is pathological in origin or the result of surgery.

16. The method of claim 15 wherein said surgery occurs at the site of a tendon.

17. The method of claim 13 wherein said administration is local.

18. The method of claim 17 wherein the local administration is intraocular or at the site of the synovial fluid at an articulating joint.

19. The method of claim 18 wherein the non-steroidal anti-inflammatory agent is a peptide.

20. The method of claim 19 wherein the peptide is cyclosporin A.

* * * * *